(12) United States Patent  
Yamazaki et al.

(10) Patent No.: US 12,086,992 B2
(45) Date of Patent: Sep. 10, 2024

(54) IMAGE PROCESSING APPARATUS, IMAGE PROCESSING SYSTEM, IMAGE PROCESSING METHOD, AND STORAGE MEDIUM FOR CLASSIFYING A PLURALITY OF PIXELS IN TWO-DIMENSIONAL AND THREE-DIMENSIONAL IMAGE DATA

(71) Applicant: CANON KABUSHIKI KAISHA, Tokyo (JP)

(72) Inventors: Fukashi Yamazaki, Kanagawa (JP); Daisuke Furukawa, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 489 days.

(21) Appl. No.: 17/341,140

(22) Filed: Jun. 7, 2021

(65) Prior Publication Data

US 2021/0295523 A1    Sep. 23, 2021

Related U.S. Application Data

(63) Continuation of application No. PCT/JP2019/049623, filed on Dec. 18, 2019.

(30) Foreign Application Priority Data

Dec. 28, 2018  (JP) ................. 2018-247775
Oct. 3, 2019   (JP) ................. 2019-183345

(51) Int. Cl.
*G06T 7/174* (2017.01)
*G06F 18/2431* (2023.01)
(Continued)

(52) U.S. Cl.
CPC .......... *G06T 7/174* (2017.01); *G06F 18/2431* (2023.01); *G06N 3/04* (2013.01);
(Continued)

(58) Field of Classification Search
CPC . G06T 7/174; G06T 7/11; G06T 7/149; G06T 7/162; G06T 7/187; G06T 7/194;
(Continued)

(56) References Cited

U.S. PATENT DOCUMENTS 9,801,601 B2 * 10/2017 Rivet-Sabourin ......... G06T 7/12
2007/0025616 A1  2/2007 Grady
(Continued)

FOREIGN PATENT DOCUMENTS

CN   107624193 A    1/2018
DE   102010028382 A1   11/2011
(Continued)

OTHER PUBLICATIONS

Fang Lu, et al.; "Automatic 3D liver location and segmentation via convolutional neural network and graph cut;" International Journal of Computer Assisted Radiology and Surgery, Springer, DE, vol. 12, No. 2, Sep. 7, 2016 (Sep. 7, 2016), pp. 171-182.
(Continued)

*Primary Examiner* — Mia M Thomas
(74) *Attorney, Agent, or Firm* — Canon U.S.A., Inc. IP Division

(57) ABSTRACT

An image processing apparatus according to the present invention includes a first classification unit configured to classify a plurality of pixels in two-dimensional image data constituting first three-dimensional image data including an object into a first class group by using a trained classifier, and a second classification unit configured to classify a plurality of pixels in second three-dimensional image data including the object into a second class group based on a result of classification by the first classification unit, the second class group including at least one class of the first class group. According to the image processing apparatus according to the present invention, a user's burden of giving
(Continued)

pixel information can be reduced and a region can be extracted with high accuracy.

29 Claims, 9 Drawing Sheets

(51) Int. Cl.

| | |
|---|---|
| G06N 3/04 | (2023.01) |
| G06N 3/08 | (2023.01) |
| G06T 7/11 | (2017.01) |
| G06T 7/149 | (2017.01) |
| G06T 7/162 | (2017.01) |
| G06T 7/187 | (2017.01) |
| G06T 7/194 | (2017.01) |
| G06V 10/25 | (2022.01) |
| G06V 10/26 | (2022.01) |
| G06V 10/44 | (2022.01) |
| G06V 10/762 | (2022.01) |
| G06V 10/774 | (2022.01) |
| G06V 10/82 | (2022.01) |
| G06V 20/64 | (2022.01) |
| G16H 30/40 | (2018.01) |

(52) U.S. Cl.
CPC ............. *G06N 3/08* (2013.01); *G06T 7/11* (2017.01); *G06T 7/149* (2017.01); *G06T 7/162* (2017.01); *G06T 7/187* (2017.01); *G06T 7/194* (2017.01); *G06V 10/25* (2022.01); *G06V 10/26* (2022.01); *G06V 10/454* (2022.01); *G06V 10/7635* (2022.01); *G06V 10/774* (2022.01); *G06V 10/82* (2022.01); *G06V 20/64* (2022.01); *G16H 30/40* (2018.01); *G06T 2200/04* (2013.01); *G06T 2207/10081* (2013.01); *G06T 2207/20072* (2013.01); *G06T 2207/20081* (2013.01); *G06T 2207/20084* (2013.01); *G06T 2207/20116* (2013.01); *G06T 2207/20161* (2013.01); *G06T 2207/30056* (2013.01); *G06T 2207/30084* (2013.01); *G06V 2201/031* (2022.01)

(58) Field of Classification Search
CPC ....... G06T 2200/04; G06T 2207/10081; G06T 2207/20072; G06T 2207/20081; G06T 2207/20084; G06T 2207/20116; G06T 2207/20161; G06T 2207/30056; G06T 2207/30084; G06T 2207/10088; G06T 2207/30096; G06F 18/2431; G06N 3/04; G06N 3/08; G06N 3/045; G06N 5/01; G06V 10/25; G06V 10/26; G06V 10/454; G06V 10/7635; G06V 10/774; G06V 10/82; G06V 20/64; G06V 2201/031; G16H 30/40; A61B 6/03

See application file for complete search history.

(56) References Cited

U.S. PATENT DOCUMENTS

| | | | |
|---|---|---|---|
| 2014/0247977 A1* | 9/2014 | Han | G06T 7/11 382/159 |
| 2015/0286786 A1* | 10/2015 | El-Baz | G06T 7/33 382/131 |
| 2016/0110632 A1* | 4/2016 | Kiraly | G06T 7/11 382/128 |
| 2016/0163048 A1* | 6/2016 | Yee | A61B 6/032 382/131 |
| 2016/0196480 A1* | 7/2016 | Heifets | G06N 3/088 382/158 |
| 2016/0203599 A1* | 7/2016 | Gillies | A61B 6/5211 382/132 |
| 2016/0300343 A1* | 10/2016 | Gazit | G16H 50/50 |
| 2018/0033144 A1* | 2/2018 | Risman | G06T 7/0014 |
| 2018/0075628 A1* | 3/2018 | Teare | G06F 18/24143 |
| 2018/0089497 A1* | 3/2018 | Romanenko | G06V 10/255 |
| 2018/0137244 A1* | 5/2018 | Sorenson | A61B 8/565 |
| 2018/0211420 A1* | 7/2018 | Yoo | A61B 6/03 |
| 2018/0247154 A1 | 8/2018 | Kitamura | |
| 2018/0315188 A1* | 11/2018 | Tegzes | G06T 7/11 |
| 2019/0065864 A1* | 2/2019 | Yu | G06V 10/764 |
| 2019/0080450 A1* | 3/2019 | Arar | G06T 7/194 |
| 2019/0237186 A1* | 8/2019 | El-Baz | G16H 30/40 |
| 2020/0320713 A1* | 10/2020 | Furukawa | G06T 7/162 |
| 2021/0133977 A1* | 5/2021 | Yamazaki | G06V 10/82 |
| 2022/0138949 A1* | 5/2022 | Enzmann | G16H 30/40 382/128 |
| 2023/0005158 A1* | 1/2023 | Lenga | G06T 7/37 |

FOREIGN PATENT DOCUMENTS

| | | |
|---|---|---|
| JP | 2007209761 A | 8/2007 |
| JP | 2009211138 A | 9/2009 |
| JP | 2013206262 A | 10/2013 |
| JP | 2014132392 A | 7/2014 |
| JP | 2014137744 A | 7/2014 |
| JP | 2016522951 A | 8/2016 |
| JP | 2017189337 A | 10/2017 |
| JP | 6407467 B1 | 10/2018 |
| WO | 2014033792 A1 | 3/2014 |
| WO | WO-2024059534 A1 * | 3/2024 |

OTHER PUBLICATIONS

Nandy Kaustav et al: "Segmentation of Nuclei From 3D Microscopy Images of Tissue via Graphcut Optimization;" IEEE Journal of Selected Topics in Signal Processing, IEEE, US, vol. 10, No. 1, Feb. 2016 (Feb. 2016), pp. 140-150.

Fukuda, Keita et al., "Automatic Segmentation of Object Region Using Graph Cuts Based on Saliency Maps and AdaBoost", The 13th IEEE International Symposium on Consumer Electronics (ISCE2009), 2009, pp. 36-37.

* cited by examiner

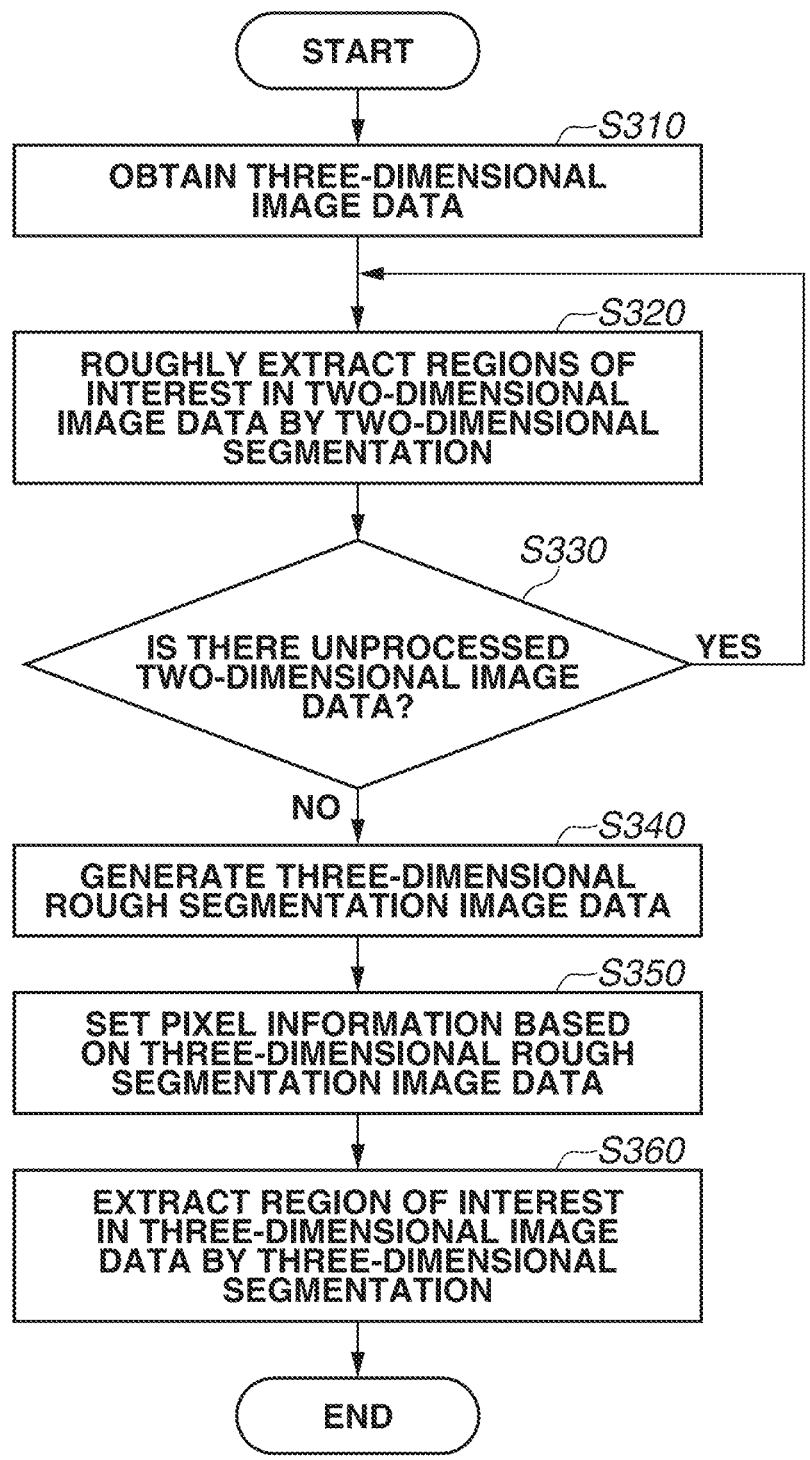

FIG.4A
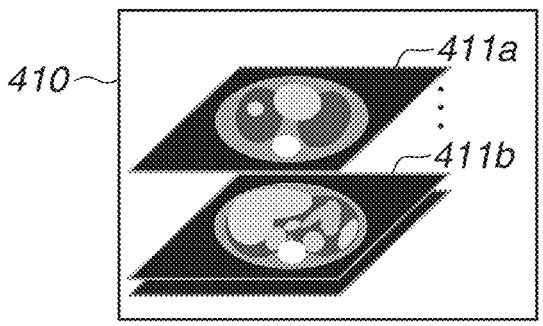
FIG.4B
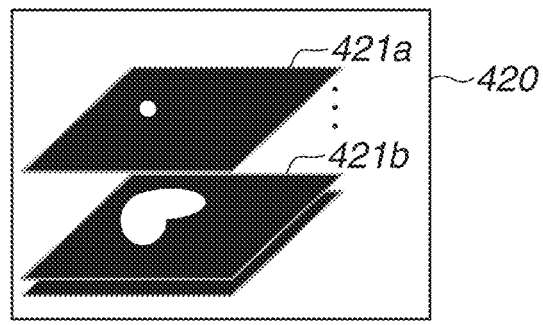
FIG.4C
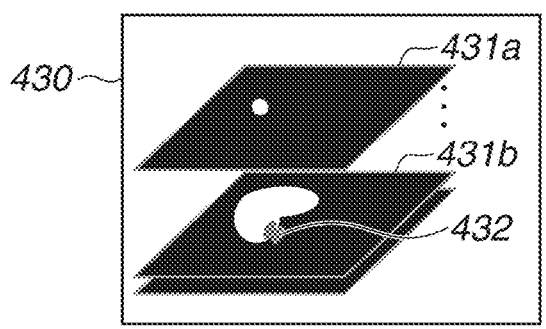
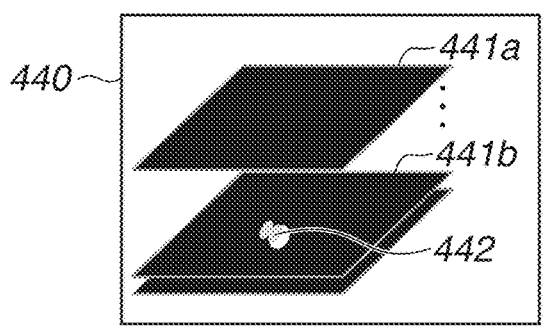
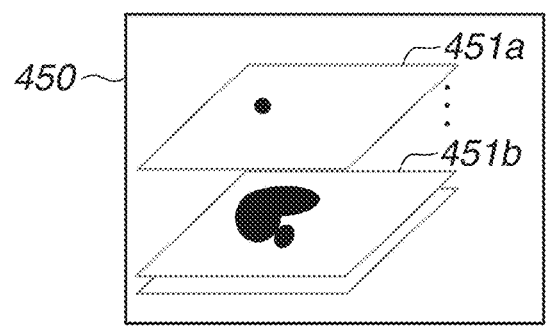
FIG.4D
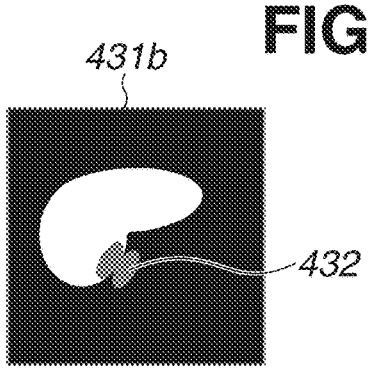
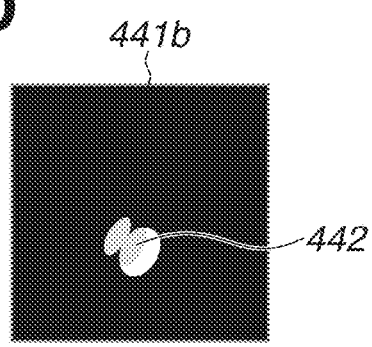

FIG.5
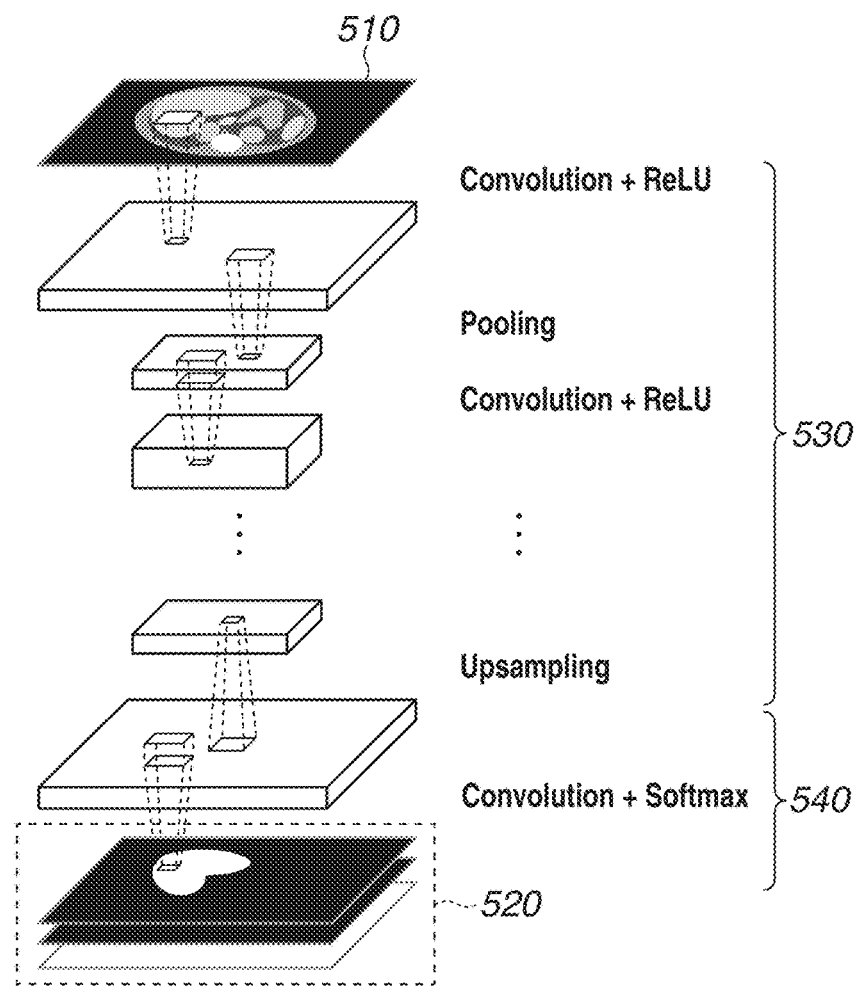
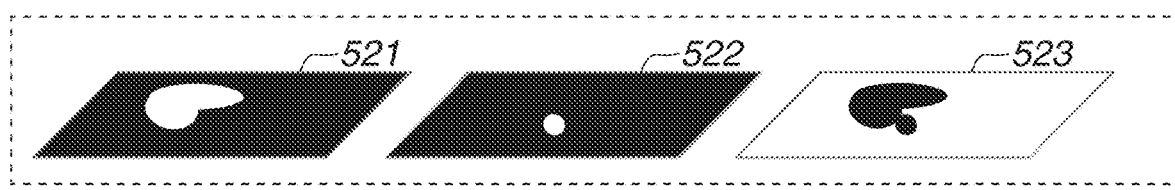

IMAGE PROCESSING APPARATUS, IMAGE PROCESSING SYSTEM, IMAGE PROCESSING METHOD, AND STORAGE MEDIUM FOR CLASSIFYING A PLURALITY OF PIXELS IN TWO-DIMENSIONAL AND THREE-DIMENSIONAL IMAGE DATA

CROSS-REFERENCE TO RELATED APPLICATIONS

This application is a Continuation of International Patent Application No. PCT/JP2019/049623, filed Dec. 18, 2019, which claims the benefit of Japanese Patent Applications No. 2018-247775, filed Dec. 28, 2018, and No. 2019-183345, filed Oct. 3, 2019, all of which are hereby incorporated by reference herein in their entirety.

BACKGROUND OF THE INVENTION

Field of the Invention

The present invention relates to an image processing apparatus, an image processing system, an image processing method, and a storage medium.

Background Art

Segmentation is one of image processing techniques. The segmentation refers to processing for distinguishing a region of interest included in an image from regions other than the region of interest, and is also called region extraction, region division, image division, etc. Many segmentation techniques have heretofore been discussed. Methods for performing segmentation with high accuracy by giving pixel information about a region of interest and regions other than the region of interest, such as discussed in Non-Patent Literature 1, have been discussed in recent years.

CITATION LIST

Non-Patent Literature

NPTL 1: Y. Boykov, and G. Funka-Lea, "Graph Cuts and Efficient N-D Image Segmentation," International Journal of Computer Vision 70(2), 109-131, 2006.

However, if segmentation is performed using the technique discussed in Non-Patent Literature 1, the user can be burdened since the user needs to give the foregoing pixel information in advance. The present invention is directed to providing an image processing apparatus that can reduce the user's burden of giving pixel information and extract a region with high accuracy.

SUMMARY OF THE INVENTION

An image processing apparatus according to the present invention includes a first classification unit configured to classify a plurality of pixels in two-dimensional image data constituting first three-dimensional image data including an object into a first class group by using a trained classifier, and a second classification unit configured to classify a plurality of pixels in second three-dimensional image data including the object into a second class group based on a result of classification by the first classification unit, the second class group including at least one class of the first class group.

Further features of the present invention will become apparent from the following description of exemplary embodiments with reference to the attached drawings.

BRIEF DESCRIPTION OF THE DRAWINGS

FIG. 3 is a flowchart illustrating an example of a processing procedure of the image processing apparatus according to the first exemplary embodiment.

FIG. 4A is a diagram for describing an example of images according to the first exemplary embodiment.

FIG. 4B is a diagram for describing an example of images according to the first exemplary embodiment.

FIG. 4C is a diagram for describing an example of images according to the first exemplary embodiment.

FIG. 4D is a diagram for describing an example of images according to the first exemplary embodiment.

FIG. 5 is a diagram for describing an example of processing by a first classification unit according to the first exemplary embodiment.

DESCRIPTION OF THE EMBODIMENTS

Figure 1:
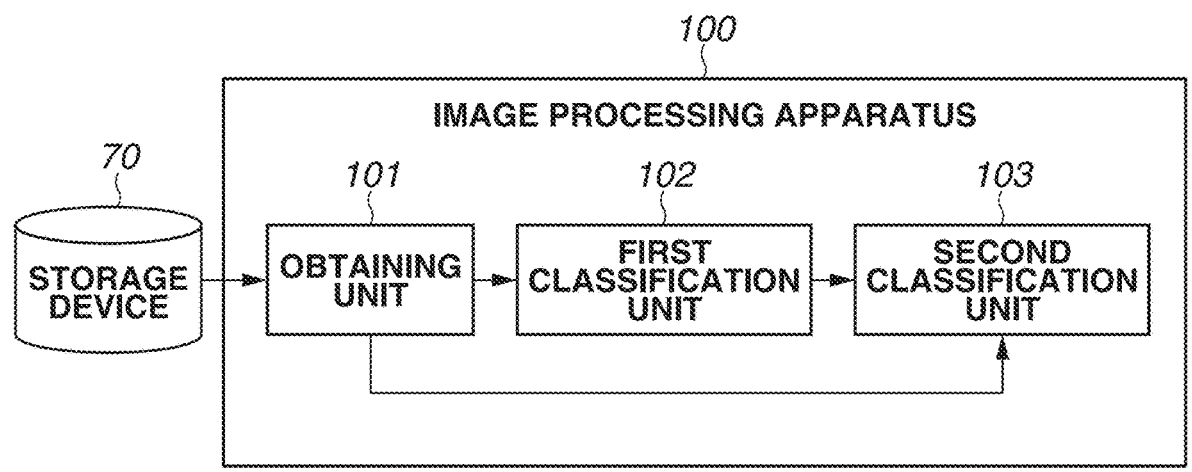
FIG. 1 is a diagram illustrating an example of a configuration of an image processing apparatus according to a first exemplary embodiment.

Exemplary embodiments of an image processing apparatus disclosed in this description will be described below with reference to the accompanying drawings. Target image data may be data of an image captured by any modality, such as an (MRI) magnetic resonance imaging device, an ultrasonic diagnostic device, or an X-ray computed tomography device, that outputs three-dimensional image data. The image processing apparatuses according to the following exemplary embodiments deal with an example of processing data of a medical image captured by an X-ray computed tomography (X-ray CT) device.

First Exemplary Embodiment

An image processing apparatus according to the present exemplary embodiment broadly extracts (roughly extracts)

regions of interest from each piece (slice) of two-dimensional image data constituting spatial three-dimensional image data (three-dimensional tomographic image) including an object by using a two-dimensional segmentation method. An example of the object is a test subject. Spatial three-dimensional image data will hereinafter be referred to as three-dimensional image data. The two-dimensional segmentation method obtains two-dimensional rough segmentation images of the regions of interest corresponding to the input two-dimensional image data. The two-dimensional rough segmentation images are then stacked or subjected to interpolation processing or integration processing to obtain a three-dimensional rough segmentation image. As employed herein, stacking refers to processing for combining two or more rough segmentation images into a continuous image. The integration processing refers to processing for integrating overlapping areas between two or more rough segmentation images into one. A more precise region of interest is then extracted using a three-dimensional segmentation method, based on the three-dimensional image data and the three-dimensional rough segmentation image obtained by the two-dimensional segmentation method. As employed herein, extracting a region refers to classifying pixels in an image into one of a predetermined class group. The classification may be made so that the position of a segmentation target can be identified, and may be intended to distinguish whether the pixel lies inside the segmentation target, such as an organ or a lesion, or distinguish whether the pixel is located on the contour of the segmentation target.

In the following example, abdominal CT images of a human body captured by an X-ray computed tomography (X-ray CT) device will be described as an example of the three-dimensional image data. Here, regions of interest in the two-dimensional segmentation method are the liver and the right kidney. In other words, the processing here is a classification problem for classifying pixels into one of a class group (hereinafter, first class group) including three classes "liver", "right kidney", and "region other than the liver and the right kidney". A region of interest in the three-dimensional segmentation method is the liver. In other words, the processing here is a problem for classifying pixels into one of a class group (hereinafter, second class group) including two classes "liver" and "region other than the liver". The configuration of this processing is intended to reduce errors (erroneous segmentation) of classifying a right kidney region as a liver region by assuming both the liver region and the right kidney region, which is likely to be erroneously extracted as the liver region, as regions of interest of the two-dimensional segmentation method. The segmentation accuracy of the liver region is expected to be improved by stacking the segmentation results obtained by the two-dimensional segmentation and using the stacked segmentation results as an input to the three-dimensional segmentation method. For the sake of convenience, a region of interest of a first classifier (two-dimensional segmentation method) will hereinafter be referred to simply as a two-dimensional region of interest. A region of interest of a second classifier (three-dimensional segmentation method) will be referred to as a three-dimensional region of interest.

In the present exemplary embodiment, a technique where the user does not necessarily need to give pixel information in advance is used as the two-dimensional segmentation method. As employed herein, pixel information refers to information including at least either position (foreground) information about a segmentation target or position (background) information about other than the segmentation target. One of segmentation methods that do not necessarily need pixel information in advance is a segmentation method based on machine learning. In machine learning, a machine learns features from given data by itself. This means, for example, that classifications can be made without the user setting a classification condition in advance in the classification problem. In the present exemplary embodiment, a CNN (Convolutional Neural Network) is used as the two-dimensional segmentation method among segmentation methods based on machine learning. As a CNN network structure, an FCN [J. Long et al., "Fully Convolutional Networks for Semantic Segmentation," In Proceedings of the IEEE Conference on Computer Vision and Pattern Recognition (CVPR), pp. 3431-3440, 2015.] is used. Any technique for performing segmentation using given pixel information, such as a region growing method, a level-set method, a graph-cut method, or a snakes method, may be used as the three-dimensional segmentation method. In the present exemplary embodiment, the graph-cut method is used.

In using a machine learning-based classifier such as a CNN, the appearance of a region of interest in a target image is preferably roughly the same even in different pieces of image data. In particular, if there is not much training data available for training the classifier and the appearance of the region of interest varies, the classifier can fail to learn variations in the appearance of the region of interest and the classification accuracy can drop.

In the case of the three-dimensional image data (X-ray CT image) according to the present exemplary embodiment, the appearance of a region of interest in the body axis direction varies due to the nature of the human body that is the test subject. Reasons for variations in the appearance of a region of interest include, for example, that the region of interest is drawn at different positions. On the other hand, axial images (axial cross-sectional images) are characterized in that a region of interest is drawn at roughly the same positions and with substantially the same resolutions even in different pieces of three-dimensional image data. Moreover, in classifying the three-dimensional image data, the accuracy of the classifier can be low depending on the images because different pieces of three-dimensional image data have different resolutions in the body axis direction. By contrast, axial images are less likely to be affected by a difference in the resolution in the body axis direction. Compared to the three-dimensional image data, the classification of two-dimensional images typified by an axial image is performed by using only two-dimensional information in three-dimensional information about the three-dimensional image data. The appearance of the segmentation target in an image during training and that during classification therefore differ less even between different pieces of three-dimensional image data if the image data based on the two-dimensional information is handled. A 2D-CNN (CNN with two-dimensional image data as an input) using a two-dimensional image, or axial image data (an example of two-dimensional image data constituting three-dimensional image data) in particular, as an input can thus reduce the burden of spatial normalization for uniformizing the appearance of the region drawn in the image.

If a 3D-CNN (CNN with three-dimensional image data as an input) is used instead of the 2D-CNN, spatial normalization such as cutting out three-dimensional spatial regions where a region of interest is and aligning the positions where the region of interest is located is needed. If the resolutions in the body axis direction are different, resolution matching processing is also performed. In general, such spatial normalization operations are difficult to apply to unknown images, and the use of the 2D-CNN makes image handling easier. The same also applies to classifiers based on non-CNN machine learning, such as an SVM (Support Vector Machine).

The image processing apparatus according to the present exemplary embodiment combines a 2D-FCN (Fully Convolutional Network) (an example of the 2D-CNN) using axial image data as an input with the graph-cut method that is a three-dimensional segmentation method. The present configuration can reduce the trouble of spatial normalization on input images and enables segmentation with three-dimensional connectivity taken into account. Note that while the segmentation method where the user does not necessarily need to give pixel information in advance is described as the two-dimensional segmentation method, the two-dimensional segmentation method may be one using pixel information given by the user as appropriate.

(Module Configuration)

A functional configuration of the image processing apparatus according to the present exemplary embodiment will be described below with reference to FIG. 1. As illustrated in the diagram, an image processing apparatus 100 according to the present exemplary embodiment include an obtaining unit 101, a first classification unit 102, and a second classification unit 103. An image processing system according to the present exemplary embodiment also includes a storage device 70 outside the image processing apparatus 100.

The storage device 70 is an example of a computer-readable storage medium. The storage device 70 is a large-capacity information storage device typified by a hard disk drive (HDD) and a solid-state drive (SSD). The storage device 70 stores at least one or more pieces of three-dimensional image data.

The obtaining unit 101 obtains three-dimensional image data from the storage device 70. The obtaining unit 101 then transmits the obtained three-dimensional image data to the first classification unit 102 as first three-dimensional image data, and to the second classification unit 103 as second three-dimensional image data.

The first classification unit 102 inputs two-dimensional image data constituting the three-dimensional image data obtained from the obtaining unit 101 (first three-dimensional image data). The first classification unit 102 then performs two-dimensional segmentation on each piece of two-dimensional image data constituting the first three-dimensional image data, whereby two-dimensional rough segmentation images corresponding to the first class group are obtained. The first classification unit further generates three-dimensional rough segmentation images by performing at least one of stacking, interpolation processing, and integration processing on the two-dimensional rough segmentation images corresponding to the first class group class by class, and transmits the three-dimensional rough segmentation images to the second classification unit 103. The two-dimensional rough segmentation images or the three-dimensional rough segmentation images obtained by performing the stacking, interpolation processing, or integration processing on the two-dimensional rough segmentation images will be referred to as a result of classification by the first classification unit 102. The result of classification corresponding to the first class group is likelihood maps expressing the likeliness of each pixel being in the class in terms of a pixel value of 0 or more and less than or equal to 1. For example, each rough segmentation image in the result of classification expresses pixels likely to be in the class by a value close to 1, and pixels unlikely to be in the class by a value close to 0. The two-dimensional rough segmentation images have the same image size as an axial image. The three-dimensional rough segmentation image has the same size as the three-dimensional image data. The pixel values in the rough segmentation images that are the result of classification may be expressed by any values that can express the likeliness of being in those classes. For example, binary values may be given as the pixel values. Different ranges of values may be given class by class. If different ranges of values are given class by class, for example, values of 0 or more and less than 1 are assigned for a first class, and values of 1 or more and less than 2 are assigned for a second class. The result of classification may be an output about which class of the class group each pixel belongs to, or an output about the likelihood of each class in the class group. The two-dimensional rough segmentation images may have the same image size as an axial image as described above, or a different image size. Similarly, the three-dimensional rough segmentation image may have the same image size as a three-dimensional image as described above, or a different image size.

In the present exemplary embodiment, the first classification unit 102 is a trained 2D-FCN. A method for training the 2D-FCN will now be described with reference to FIGS. 6A and 6B. A 2D-FCN is one of supervised training models among machine learning models. A machine previously trained with two-dimensional ground truth images and two-dimensional training images in association with each other exerts classification ability. Here, a ground truth image including a plurality of two-dimensional ground truth images and a training image including a plurality of two-dimensional training images will be referred to collectively as training data.

Figure 6A:
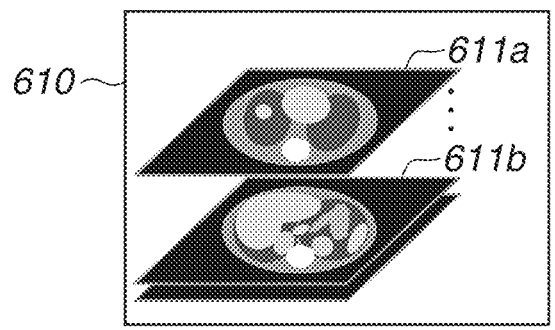
FIG. 6A is a diagram for describing an example of training data for the first classification unit according to the first exemplary embodiment.
Figure 6B:
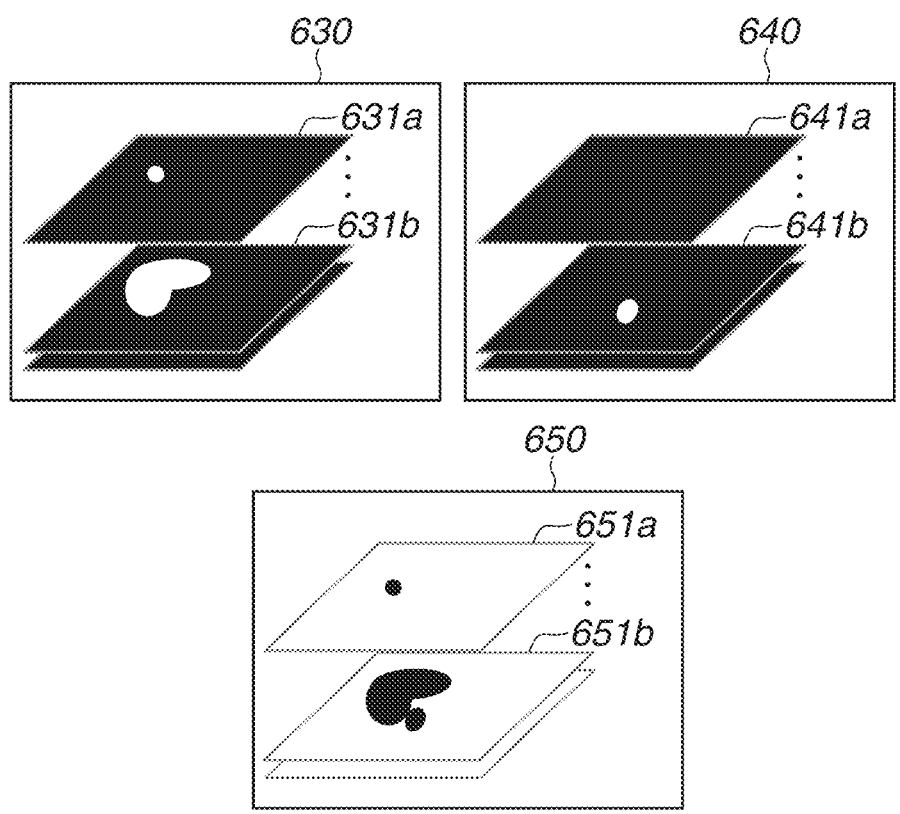
FIG. 6B is a diagram for describing an example of the training data for the first classification unit according to the first exemplary embodiment.

FIGS. 6A and 6B illustrate training data in training the 2D-FCN. FIG. 6A illustrates a training image 610 that is a set of two-dimensional axial images. In the present exemplary embodiment, the training image 610 is a set of abdominal CT images captured by the X-ray CT device. The training image 610 includes an axial image 611a and an axial image 611b. FIG. 6B illustrates sets of two-dimensional ground truth images corresponding to the respective classes in the first class group of the training image 610. In the present exemplary embodiment, a liver region, a right kidney region, and a region other than the liver and the right kidney are classified. Ground truth images corresponding to the respective classes include a plurality of two-dimensional ground truth images each. Specifically, the ground truth images include a ground truth image 630 of the liver region, a ground truth image 640 of the right kidney region, and a ground truth image 650 of the region other than the liver and the right kidney. Each ground truth image, for example, the ground truth image 630 of the liver region includes a two-dimensional ground truth image 631a of the liver region corresponding to the axial image 611a and a two-dimensional ground truth image 631b of the liver region corresponding to the axial image 611b. Similarly, the ground truth image of the right kidney region includes a two-dimensional ground truth image 641a of the right kidney region corresponding to the axial image 611a and a two-dimensional ground truth image 641b of the right kidney region corresponding to the axial image 611b. The ground truth image of the region other than the liver and the right kidney includes a two-dimensional ground truth image 651a and a two-dimensional ground truth image 651b.

The ground truth image corresponding to each class of the first class group includes the pixels expressing whether the pixels are in that class by binary values, and is characterized by the absence of overlapping areas between the ground truth images corresponding to the respective classes. The 2D-FCN is trained by using a training data set including one or more pieces of training data described above. For example, backpropagation that is a typical technique in CNN training is used as a training method. The 2D-FCN is thereby trained with features for classifying regions of interest, and becomes capable of extracting the regions of interest even from unknown images. The ground truth image may be an image expressing whether the pixels are in the class by binary values as described above, or an image where the pixels express the likeliness of being in the class by continuous values. If the ground truth image is an image expressing the likeliness of being in the class by continuous values, the first classification unit 102 is configured to solve a regression problem for each pixel.

The second classification unit 103 inputs the three-dimensional image data obtained from the obtaining unit 101 (second three-dimensional image data) and the three-dimensional rough segmentation images corresponding to the respective classes obtained from the first classification unit 102, and outputs a three-dimensional image of interest corresponding to the second class group. The three-dimensional image of interest is an image expressing the likeliness of being a region to be extracted, and its pixel values are expressed as in the foregoing three-dimensional rough segmentation images.

Note that at least some of the components of the image processing apparatus 100 illustrated in FIG. 1 may be implemented as independent devices. Alternatively, such components may be implemented as software for implementing the respective functions. In the present exemplary embodiment, the components are implemented by respective pieces of software.

(Hardware Configuration)

Figure 2:
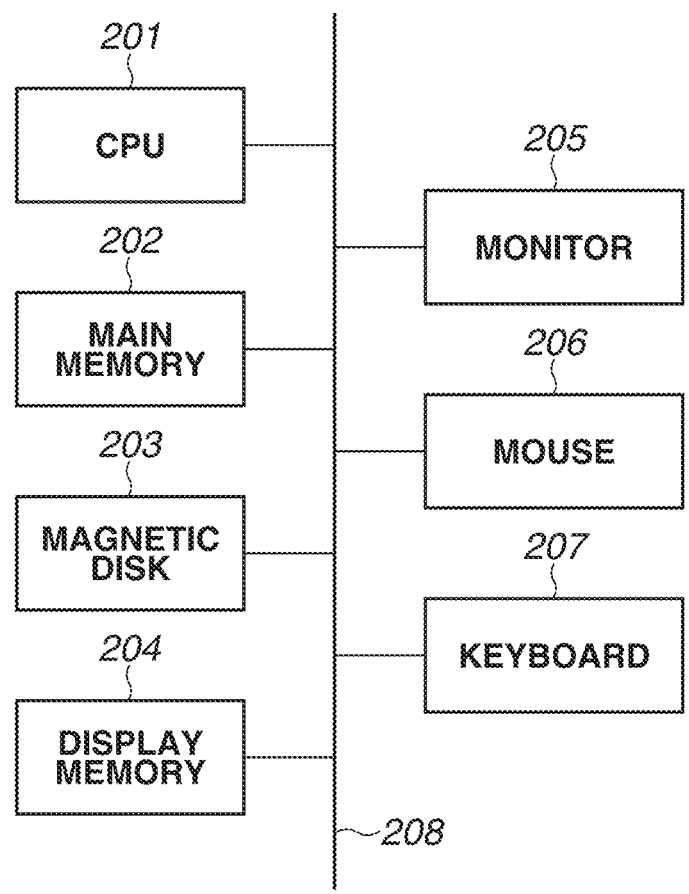
FIG. 2 is a diagram illustrating an example of a hardware configuration of the image processing apparatus according to the first exemplary embodiment.

FIG. 2 is a diagram illustrating an example of a hardware configuration of the image processing apparatus 100. A CPU (Central Processing Unit) 201 mainly controls operation of the components. A main memory 202 stores a control program to be executed by the CPU 201, and provides a work area when the CPU 201 executes a program. A magnetic disk 203 stores an OS (Operating System), device drivers of peripheral devices, and programs for implementing various types of application software, including a program for performing processing to be described below, etc. The CPU 201 executes the programs stored in the main memory 202 and the magnetic disk 203, whereby the functions (software) of the image processing apparatus 100 illustrated in FIG. 1 and processing of a flowchart to be described below are implemented.

A display memory 204 temporarily stores display data. A monitor 205 is a CRT monitor, a liquid crystal monitor, or the like, for example. The monitor 205 displays images, text, and the like based on data from the display memory 204. A mouse 206 and a keyboard 207 performs user's pointing input and character input or the like. Such components are mutually communicably connected by a common bus 208.

The CPU 201 corresponds to an example of a processor. The image processing apparatus 100 may include at least either a GPU (Graphics Processing Unit) or an FPGA (Field-Programmable Gate Array) in addition to the CPU 201. The image processing apparatus 100 may include at least either a GPU or an FPGA instead of the CPU 201. The main memory 202 and the magnetic disk 203 correspond to an example of a memory.

(Processing Flow)

Next, a processing procedure of the image processing apparatus 100 according to the present exemplary embodiment will be described with reference to FIG. 3.

<Step S310: Step of Obtaining Three-Dimensional Image Data>

In step S310, the obtaining unit 101 obtains three-dimensional image data from the storage device 70.

<Step S320: 2D-FCN Based Classification Step>

In step S320, the first classification unit 102 extracts two-dimensional regions of interest from each of the two-dimensional axial images constituting the three-dimensional image data by using the two-dimensional segmentation method. The two-dimensional regions of interest are output as two-dimensional rough segmentation images corresponding to the respective classes of the first class group. In the present exemplary embodiment, the first classification unit 102 is a trained 2D-FCN for classifying pixels into the three classes, i.e., the liver, the right kidney, and other than the liver and the right kidney.

The input and output of the 2D-FCN will be described with reference to FIG. 4A to 4D. FIG. 4A illustrates three-dimensional image data 410 obtained in step S310. In FIG. 4A, the three-dimensional image data 410 includes a plurality of axial images such as an axial image 411a and an axial image 411b. Each of such axial images is input to the 2D-FCN. FIG. 4C illustrates three-dimensional rough segmentation images corresponding to the respective classes. A three-dimensional rough segmentation image 430 of the liver region, a three-dimensional rough segmentation image 440 of the right kidney region, and a three-dimensional rough segmentation image 450 of the region other than the liver and the right kidney are illustrated in FIG. 4C. In FIG. 4C, the regions of the respective classes are illustrated in light color, and the regions other than those of the respective classes are in dark color. Each three-dimensional rough segmentation image includes two-dimensional rough segmentation images corresponding to the respective axial images that are the input of the 2D-FCN. For example, in the three-dimensional rough segmentation image 430 of the liver region, a two-dimensional rough segmentation image 431a of the liver region is a two-dimensional rough segmentation image corresponding to the axial image 411a, and a two-dimensional rough segmentation image 431b of the liver region is one corresponding to the axial image 411b. If an axial image is input by processing to be described below, the 2D-FCN outputs two-dimensional rough segmentation images corresponding to the respective classes. A rough segmentation image 441a and a rough segmentation image 441b of the right kidney region correspond to the axial image 411a and the axial image 411b of the three-dimensional image data 410, respectively. Similarly, a rough segmentation image 451a and a rough segmentation image 451b of the region other than the liver and the right kidney correspond to the axial image 411a and the axial image 411b, respectively.

The processing of the 2D-FCN will be described with reference to FIG. 5. If an input image 510 (axial image) is input to the 2D-FCN, convolution processing, pooling processing, and upsampling processing are performed a plurality of times in an intermediate layer 530. In an output layer 540, convolution processing is then performed, and the output values of the respective pixels are normalized by softmax processing, whereby output images 520 that are two-dimensional images containing classification information about the pixels are obtained.

Here, the convolution processing extracts features while maintaining the shape of the image. The pooling processing reduces the spatial size, i.e., the width and height of the image to expand the receptive field. The upsampling obtains detailed resolution using pooling information. The output images 520 include two-dimensional rough segmentation images of the number that is the same as the number of classes to be classified. In the present exemplary embodiment, the output images 520 include a two-dimensional rough segmentation image 521 of the liver region, a two-dimensional rough segmentation image 522 of the right kidney region, and a two-dimensional rough segmentation image 523 of the region other than the liver and the right kidney. A model including convolution processing, pooling processing (encoder), and upsampling processing (decoder) as a network structure, typified by an FCN, is referred to as an encoder-decoder model. Encoders retain global information while allowing some displacements of pixels. Decoders restore resolution while maintaining feature amounts resulting from the encoders. Such a model is expected to provide a certain accuracy even if the position of the segmentation target varies between pieces of two-dimensional image data constituting different pieces of three-dimensional image data. The network structure is not limited to only this structure as long as the network structure has an architecture capable of processing image information in a multi-scale fashion.

Now, the softmax processing will be described by using an equation. Assuming that a pixel value before the softmax processing is $a_{i,j,k}$, a pixel value $p_{i,j,k}$ after the softmax processing is calculated based on the following Eq. (1):

[Eq. 1]

$$p_{i,j,k} = \frac{\exp(a_{i,j,k})}{\sum_{m}^{K} \exp(a_{i,j,m})} \quad \text{Eq. (1)}$$

Here, i and j represent pixel numbers for identifying a pixel in a two-dimensional rough segmentation image. k represents a number corresponding to the rough segmentation image of each class. K represents the number of classes to be classified. Since the present exemplary embodiment deals with a three-class problem with the liver region, the right kidney region, and the region other than the liver and the right kidney, K=3. This processing makes the summation of the pixel values in the results of classification corresponding to the respective classes 1. In other words, each of the two-dimensional rough segmentation images corresponding to the respective classes is a two-dimensional likelihood map expressing the likeliness of that region.

(Variation of First Classification Unit)

The rough segmentation images that are the output of the first classification unit 102 do not need to be ones where each pixel is expressed in terms of likelihood indicating the likeliness of being in that class as described above. For example, the value of each pixel may be expressed by binary values or expressed by a different range of values class by class. The values obtained from the first classification unit may be directly used as the values of the pixels. The numerical values may be converted by using a threshold or thresholds.

The first classification unit 102 may be a CNN different from the foregoing 2D-FCN. The first classification unit 102 is not limited to a CNN and may be a classifier based on any two-dimensional segmentation method as long as the classifier extracts a region of interest from each axial image. For example, a classifier based on non-CNN machine learning (SVM, k-means, boosting, and random forest) or a classifier that does not need training, like a thresholding classifier, may be used. The first classification unit may include a plurality of classifiers. The plurality of classifiers may be used in parallel or hierarchically.

The first classification unit 102 is not limited to a classifier that simultaneously performs classification into three or more classes as described above, either. For example, the first classification unit 102 may be a classifier for performing classification into two classes, the liver region and the region other than the liver region. A plurality of classifiers for two-class classification may be prepared to obtain rough segmentation images from the respective classifiers. In a specific example, the same results as the foregoing processing can be obtained by preparing a classifier for classifying the liver region and others and a classifier for classifying the right kidney and others.

<Step S330: Processing End Determination Step>

In step S330, the first classification unit 102 determines whether there is unprocessed two-dimensional image data to be processed in the three-dimensional image data. If there is unprocessed two-dimensional image data, the processing proceeds to step S320. In step S320, the first classification unit 102 performs rough segmentation of the regions of interest. If there is no unprocessed two-dimensional image data, the processing proceeds to the next step.

<Step S340: Three-Dimensional Rough Segmentation Image Generation Step>

In step S340, the first classification unit 102 serving as a three-dimensional data generation unit generates three-dimensional rough segmentation images by stacking or performing the interpolation processing or integration processing on the two-dimensional rough segmentation images corresponding to the respective classes obtained by the processing up to step S330. The first classification unit 102 then outputs the generated three-dimensional rough segmentation images to the second classification unit 103. The three-dimensional rough segmentation images correspond to a three-dimensional result of classification. Note that the function of the three-dimensional data generation unit for generating the three-dimensional rough segmentation images may be implemented by the second classification unit 103 or by a calculation unit other than the first classification unit 102 and the second classification unit 103.

In the present exemplary embodiment, the classification technique that the second classification unit 103 to be described below performs is a graph-cut method for classifying the pixels into two classes, the liver and other than the liver. The graph-cut method constructs a graph based on pixel information about the region to be extracted (foreground) and the regions other than the region to be extracted (background), and extracts the region to be extracted so that a designed energy function is minimized (or maximized). An energy function E of the graph-cut method is typically defined as the following Eq. (2):

[Eq. 2]

$$E = \sum_{i \in Node} E_1(i) + \lambda \times \sum_{(i,j) \in Edge} E_2(i, j) \quad \text{Eq. (2)}$$

In the foregoing Eq. (2), i and j represent respective different pixel numbers in the image. $\lambda$ is a constant parameter for adjusting the degrees of contribution of a data term $E_1$ and a smoothening term $E_2$.

<Step S350: Pixel Information Setting Step>

Figure 7A:
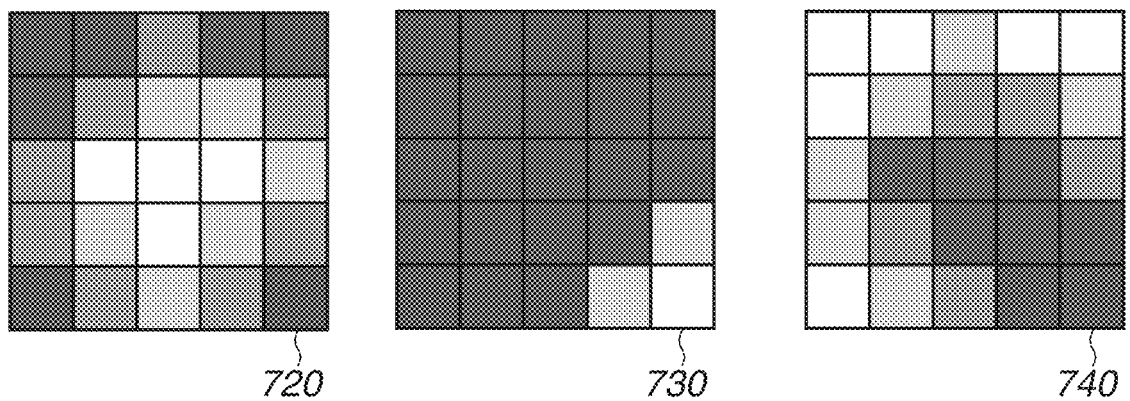
FIG. 7A is a diagram for describing an example of an output of the first classification unit according to the first exemplary embodiment.
Figure 7B:
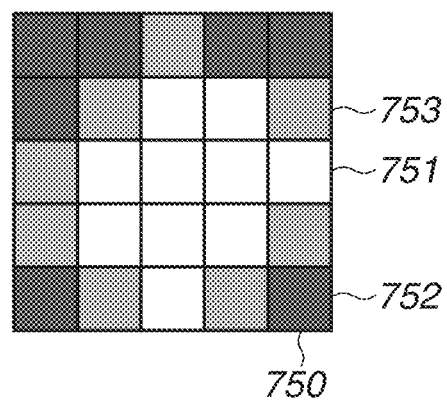
FIG. 7B is a diagram for describing an example of the output of the first classification unit according to the first exemplary embodiment.

The second classification unit 103 sets pixel information indicating the positions of pixels corresponding to at least either the foreground or the background based on the three-dimensional rough segmentation images. The setting of the pixel information will be described with reference to FIGS. 7A and 7B. Here, how to give pixel information about the liver region that is the foreground and the regions other than the liver region that are the background in extracting the liver region will be described. For ease of description, two-dimensional images are used here for illustration. FIG. 7A illustrates a rough segmentation image 720 of the liver region, a rough segmentation image 730 of the right kidney region, and a rough segmentation image 740 of the region other than the liver and the right kidney, each of which is a rough segmentation image with five pixels on each side. The pixel values of the rough segmentation images according to the present exemplary embodiment vary continuously since the pixel values indicate likelihood representing the likeliness of being in the respective classes. In the present exemplary embodiment, the rough segmentation images corresponding to the three classes are thus compared pixel by pixel, and pixels where the likelihood of the liver is higher than that of the other classes among the likelihood of the liver, the likelihood of the right kidney, and the likelihood of other than the liver and the right kidney are set as foreground pixels (pixels determined as the foreground). Similarly, pixels where the likelihood of the liver is lower than that of the other classes are set as background pixels (pixels determined as the background). The remaining pixels (such as pixels where the likelihood of the liver is the second highest) are set as intermediate pixels (whether the pixels are the foreground or background is not yet to be determined). FIG. 7B illustrates a seed image 750 obtained by integrating the rough segmentation images by the method described above. The seed image 750 includes foreground pixels 751, background pixels 752, and intermediate pixels 753. In the present exemplary embodiment, the energy function expressed by Eq. 2 is defined based on the seed image 750. Specifically, the data term $E_1$ sets the energy of each pixel depending on a distance value based on the foreground pixels 751 and the background pixels 752 in the seed image 750. The energy is set to give sufficiently high cost to corresponding edges (t-link) of the pixels in the graph so that foreground pixels 751 and the background pixels 752 remain the foreground and background pixels, respectively, (remain unchanged) even after the segmentation by the graph-cut method. The smoothening term $E_2$ sets energy based on differences in a voxel value between adjoining pixels in the three-dimensional image data 410. By thus defining the energy function, the intermediate pixels 753 are classified into either the foreground or the background. The second classification unit 103 then divides the region to be extracted and the regions other than the region to be extracted by assuming that the pixels classified as the foreground are in the region to be extracted and the pixels classified as the background are in the regions other than the region to be extracted.

Any method that determines at least either the foreground pixels or the background pixels based on the rough segmentation images obtained from the first classification unit 102 may be used as the method for setting the pixel information. For example, the second classification unit may determine either one (the foreground or background) pixels based on the rough segmentation images, and determine the other (background or foreground) pixels based on the pixel values of the three-dimensional image data. In the foregoing method, in determining whether the pixels are in the foreground or the background based on the rough segmentation images, the determinations are made based on a relationship in magnitude between the likelihood of the liver and that of other than the liver. However, this is not restrictive. For example, foreground pixels may be first determined, and pixels a predetermined distance (distance value) or more away from the determined foreground pixels may be determined as background pixels. Alternatively, foreground (or background) pixels may be determined by threshold processing, referring to only the rough segmentation image of the liver. The second classification unit can thereby determine the foreground pixels and the background pixels and further determine the remaining pixels as intermediate pixels even if the first classification unit is a classifier for two-class classification.

While in the foregoing method the energy of each pixel is set based on the distance value, the energy of each pixel may be set based on the likelihood in the rough segmentation images. In the foregoing method, the energy is set to give sufficiently high cost to corresponding edges (t-link) of the pixels in the graph so that the foreground pixels and the background pixels will not be changed by the graph-cut method. However, this is not restrictive. For example, the magnitude of likelihood may be set as energy with which the foreground or background pixels can change. The energy may be set based on the likelihood and the distance value.

Moreover, the foreground, background, and intermediate pixels in the seed image may be set based on the magnitude of likelihood. For example, in the foregoing method for setting the foreground and background pixels, the rough segmentation images corresponding to the respective classes are described to be initially compared pixel by pixel. A target pixel is then set as the foreground if the likelihood of the liver is the highest, and set as the background if the likelihood of the liver is the lowest. However, if the likelihood of the respective classes is similar, simply comparing the likelihood of the pixels and determining at least either the foreground or the background can fail to provide sufficient accuracy. In view of this, for example, a predetermined threshold may be provided for the likelihood. If the predetermined threshold is satisfied, either the foreground or the background may be set. Pixels that do not satisfy the predetermined threshold may be set as intermediate pixels. The predetermined threshold for the likelihood may be combined with the foregoing pixel-by-pixel comparison result of the rough segmentation images corresponding to the respective classes.

If the likelihood does not satisfy the predetermined threshold or if the pixel-by-pixel comparison between the classes shows that the likelihood of the liver is neither higher than that of the other pixels nor lower than that of the other pixels, that pixel is set as an intermediate pixel. The information about the foreground and the background is then given to the data term $E_1$ in the graph-cut energy function, and segmentation is performed. Here, pixels other than the foreground or background pixels are regarded as intermediate pixels and classified by a graph cut.

Foreground, background, and intermediate pixels are set based on at least either the magnitudes of the likelihood or the pixel-by-pixel likelihood comparison. Sufficiently high energy is set for corresponding edges (t-link) of the pixels so that the foreground and background pixels will not be changed by the graph-cut method. Here, the likelihood of the intermediate pixels is further given to the graph-cut energy function. Such a configuration enables the intermediate pixels to be classified by a graph cut to add the information based on the features learned by the classifier, and the segmentation accuracy is expected to be improved. More specifically, foreground, background, and intermediate pixels are set, and first energy and second energy both of which are sufficiently high are set for the edges (t-link) of the foreground and background pixels. Third energy corresponding to the likelihood of output from the classification unit 102 is set for an intermediate region.

<Step S360: Step of Extracting Region of Interest by Graph-Cut Method>

The second classification unit 103 extracts a region to be extracted from the three-dimensional image data by the three-dimensional segmentation method based on the pixel information obtained in step S350. The second classification unit 103 then outputs information about the extracted region to be extracted to the magnetic disk 203 and the external storage device 70 as a three-dimensional image of interest 420 illustrated in FIG. 4B. The image of interest 420 includes an image of interest 421*a* and an image of interest 421*b*.

Now, a difference between the three-dimensional rough segmentation image 430 of the liver region that is one of the outputs of the first classification unit 102 and the three-dimensional image of interest 420 that is the output of the second classification unit 103 will be described with reference to FIGS. 4A to 4D. As illustrated in FIG. 4D (enlarged view of rough segmentation images), the two-dimensional rough segmentation image 431*b* of the liver region and the two-dimensional rough segmentation image 441*b* of the right kidney region include a region 432 and a region 442 of high likelihood, respectively, near the border between the liver region and the right kidney region. Here, the region 432 and the region 442 are regions representing the same region in the three-dimensional image data. Suppose that, in this region, the likelihood indicating the likeliness of being the right kidney is the highest (light color) and the likelihood indicating the likeliness of being the liver is the second highest in the three three-dimensional rough segmentation images that are the output of the first classification unit 102. In such a case, the region corresponds to intermediate pixels. The region is therefore one to be classified into either the foreground or the background by the graph-cut method. Since the graph-cut method tends to divide regions along edges nearby, the region 432 can be removed from the liver region (FIG. 4B).

Note that if the second classification unit uses the graph-cut method, the second classification unit may be configured to perform classification into the second class group by using the first energy (foreground), the second energy (background), and the third energy (intermedia pixels) set in step S350.

(Variation of Second Classification Unit)

The second classification unit 103 may use any three-dimensional segmentation method based on pixel information about at least either the foreground or the background. Examples of other segmentation methods may include a region growing method, a snake method, and a level-set method. In the region growing method, pixel positions of the region to be extracted need to be given. For that purpose, the positions where the foreground pixels 751 are can be given as the pixel positions of the region to be extracted, for example. In the cases of the snake method and the level-set method, coordinate data on the contour of the region to be extracted needs to be given as initial values. For that purpose, for example, the border pixels of the foreground pixels 751 in FIG. 7B can be given as initial values. To extract the contour, a classifier trained with contours and other than contours can be used for extraction. While in the present exemplary embodiment the second classification unit 103 uses the three-dimensional segmentation method for classifying the pixels into two classes, a method for classifying pixels into three or more classes may be used.

Effect of First Exemplary Embodiment

As described above, the image processing apparatus 100 according to the first exemplary embodiment roughly extracts regions of interest from each piece of two-dimensional axial image data constituting three-dimensional image data by the two-dimensional segmentation method using machine learning. The image processing apparatus 100 then extracts a three-dimensional region of interest by the three-dimensional segmentation method based on the three-dimensional image data and three-dimensional rough segmentation images. Since such a configuration can automatically give pixel information about the regions of interest and the regions other than the regions of interest to the three-dimensional segmentation method, the user's burden of inputting pixel information can be reduced. Moreover, since images where the regions of interest are located at positions that are roughly the same as those of the regions of interest in the training images can be input, the regions of interest can be extracted with high accuracy.

Modifications

In the image processing apparatus 100 according to the foregoing first exemplary embodiment, three-dimensional image data that is the same as the original three-dimensional image data is input to the first classification unit 102 and the second classification unit 103. However, three-dimensional image data different from the original three-dimensional image data may be input. The obtaining unit 101 may include a calculation unit for that purpose. The calculation unit may be included in a unit other than the obtaining unit, or may include a plurality of calculation units. The image processing apparatus 100 may include the calculation unit aside from the obtaining unit 101. Before the different three-dimensional image data is input to the first classification unit and the second classification unit, the obtaining unit 101 may perform noise reduction, normalization of voxel values, spatial normalization, and/or image resizing on the original three-dimensional image data, for example. Such processes may be common between the classification units, or different processes may be performed for the inputs of the respective classification units. In the former case, the first three-dimensional image data and the second three-dimensional image data are the same images. In the latter case, the first three-dimensional image data and the second three-dimensional image data are different images. If, for example, the input images to the classification units are spatially normalized differently, a modification unit for normalizing the output of the first classification unit 102 to the input space of the second classification unit 103 is needed. Since such a configuration can input three-dimensional image data based on the characteristics of each classifier, the segmentation accuracy of the regions of interest is expected to be improved. If the first classification unit 102 performs classification based on machine learning, processing for reducing resolution can preferably be performed depending on restrictions such as calculation time, memory capacity, and image size during training. In such a case, the first three-dimensional image data is configured to have resolution lower than that of the second three-dimensional image data.

Note that the foregoing processes may be performed only on the input of either one of the classification units. If the object is the same test subject, past additional information may be referred to and three-dimensional image data captured at a different time may be used. For example, an image captured of the subject at a time phase is input to the first classifier, and an image captured at another time phase is input to the second classifier. In other words, the first three-dimensional image data and the second three-dimensional image data are pieces of three-dimensional image data that are linked with the same test subject and have different imaging times. Such a configuration is expected to improve the segmentation accuracy by referring to different time phases, for example, compared to a case where the regions of interest are extracted only from information about a result of a single imaging operation.

As another modification, a calculation unit or a modification unit may apply processing for removing components other than a largest connected component to the rough segmentation images of the regions of interest that are the output of the first classification unit 102 or the three-dimensional image of interest that is the output of the second classification unit 103. The largest connected component refers to the largest region among regions where pixels are continuous. Moreover, small isolated regions may be deleted by applying opening processing or closing processing or by applying processing for deleting regions other than a largest connected component. If the number of regions of interest to be drawn in the three-dimensional image data is one, the segmentation accuracy of the region of interest improves since needless regions can thereby be removed. Other preprocessing and postprocessing may be used in combination.

The segmentation target may be any organ other than the liver and may be a cyst, a tumor, a node, a contour of these, or the like, as long as the segmentation target is a region expressed on an image. Moreover, the classes of the training data and the segmentation targets of the first classification unit do not need to be the liver, the right kidney, and other than the liver and the right kidney as in the present exemplary embodiment. For example, classes may include organs close to the segmentation target and having similar CT values, like the liver and the right kidney. A class may include a non-organ object such as a bone.

If the second classifier is one for performing classification into the liver and other than the liver, for example, the number of classes (the liver, the right kidney, and other than the liver and the right kidney) constituting the class group of the first classifier is configured to classify more classes than the number of classes constituting the class group of the second classifier. Such a configuration is expected to improve the segmentation accuracy of the liver region since the results of classification by the first classifier provide classifications based on the features of a greater number of classes.

Furthermore, the training data and the segmentation targets of the first classification unit 102 may be changed depending on the configuration and the segmentation target of the second classification unit 103. For example, if the second classification unit 103 uses the level-set method or the snake method, the border pixels of the regions of interest can be used as training data for the first classification unit. In such a case, the first classification unit roughly extracts the border pixels, and the second classification unit 103 extracts an image based on the rough segmentation images.

If the segmentation accuracy of the first classification unit is insufficient due to lack of training data, the training data may be augmented. As described above, the machine learning includes learning features from training data, and the classification ability is exerted based on the features. On the other hand, if, for example, an organ changes in shape or has different voxel values because of a lesion, the number of pieces of training data can be not sufficient to perform classification with high accuracy. In such a case, data can be augmented to provide a sufficient number of pieces of training data by data augmentation such as shifting voxel values and making rotation and translation, or using a GAN (Generative Adversarial Network). Training the classifiers with the obtained training data on lesions and the like with different shapes and voxel values enables highly versatile segmentation. The training data with different shapes and voxel values may be used to train classifiers that are the same as those trained with images of typical organs and the like, or separately train different classifiers. In the case of different classifiers, the image processing apparatus 100 may include an additional processing unit for determining which to use for classification, the classifiers trained with images of ordinary organs and the like or the classifiers trained with the training data of different shapes and voxel values. Alternatively, the image processing apparatus 100 may have a hierarchical structure to use different classifiers based on the result of classification by a classifier trained with images of ordinary organs and the like. The image processing apparatus 100 may have a structure to use a classifier trained with images of ordinary organs and the like based on the results of classification by different classifiers. For example, if the classification targets of a training device are a liver having a different shape or voxel value and a normal liver, the ground truth labels may be different or the same. The labels may be changed based on the presence or absence or the characteristics of other classes. If segmentation is performed using a plurality of classifiers, the classes are not limited to ones including the same organs. If classification is hierarchically performed using a plurality of classifiers, for example, the liver may be initially extracted and then the right kidney may be extracted based on the segmentation result of the liver.

Second Exemplary Embodiment

In the image processing apparatus according to the first exemplary embodiment, the first classification unit uses the two-dimensional segmentation method of inputting each piece of two-dimensional image data constituting three-dimensional image data. However, extracting regions of interest from two-dimensional image data can lower the segmentation accuracy of the regions of interest if the regions of interest are drawn as small regions on the two-dimensional image data or if another region near a region of interest has voxel values similar to those of the region of interest. Moreover, the use of the two-dimensional segmentation method based on machine learning can lower the segmentation accuracy if a region of interest has an unusual shape. By contrast, three-dimensional image data has the advantage that voxels containing information about connections between the two-dimensional images can be used. Simply classifying three-dimensional image data, however, can fail to provide sufficient segmentation accuracy if the region of interest in the target image varies in appearance or if the resolution is different. Moreover, the number of images of medical image data is often insufficient.

An image processing apparatus according to a second exemplary embodiment then uses three-dimensional spatial regions having a predetermined size as training data for a classification unit. As employed herein, the predetermined size refers to a three-dimensional spatial region including two or more pieces of two-dimensional image data in the three-dimensional image data. Note that the two-dimensional image data constituting the three-dimensional spatial region having the predetermined size does not need to include continuous slices. For example, two-dimensional slices constituting a three-dimensional spatial region of higher resolution among pieces of three-dimensional image data having different resolutions may be thinned out by a predetermined number, and the resulting slices may be used as training data. The training data having the predetermined size is expected to provide the effect of reducing the time and effort for processing for matching the image size during training with that during classification (spatial normalization) while maintaining the number of pieces of training data. A first classification unit initially inputs each of three-dimensional spatial regions having the predetermined size (an example of a first three-dimensional spatial region and a second three-dimensional spatial region) in the three-dimensional image data, and roughly extracts regions of interest. Here, the trained first classifier desirably matches the size of the training data to be input. For that purpose, for example, the image processing apparatus may include a storage device for storing at least one of the number of pixels, the number of voxels, and the number of slices that indicate the input size of the images used during the training. The size of the input image to the classification unit is then determined based on the stored input size during the training. For example, if the size of the image to be classified is greater than the input size during the training, the image can be decimated to be used as the input image. On the other hand, if the size of the image to be classified is smaller than the input size during the training, additional interpolation processing is performed to obtain the input image.

In the present exemplary embodiment, rough segmentation images corresponding to each three-dimensional spatial region are obtained. The rough segmentation images are thus further stacked or subjected to interpolation processing or integration processing to obtain three-dimensional rough segmentation images. Like the first exemplary embodiment, the region to be extracted is extracted by a three-dimensional segmentation method based on the three-dimensional image data and the three-dimensional rough segmentation images obtained by the first classification unit. In the present exemplary embodiment, a 3D-FCN for processing three-dimensional image data is used since the input to the first classification unit is a three-dimensional spatial region. Differences from the first exemplary embodiment will now be described.

(Module Configuration)

The image processing apparatus according to the present exemplary embodiment has a configuration similar to that of the image processing apparatus 100 according to the first exemplary embodiment. A functional configuration of the image processing apparatus according to the present exemplary embodiment will thus be described with reference to FIG. 1, with portions overlapping the image processing apparatus according to the first exemplary embodiment omitted.

The components of an image processing apparatus 100 will be described below.

An obtaining unit 101 performs processing similar to that of the obtaining unit 101 according to the first exemplary embodiment.

A first classification unit 102 performs three-dimensional processing on each of three-dimensional spatial regions having the predetermined size, constituting the three-dimensional image data obtained from the obtaining unit 101, and thereby obtains rough segmentation images of the three-dimensional spatial region corresponding to the respective classes. The first classification unit then generates three-dimensional rough segmentation images corresponding to the respective classes by stacking the rough segmentation images of the three-dimensional spatial region corresponding to the respective classes class by class, and transmits the three-dimensional rough segmentation images to a second classification unit.

The second classification unit 103 performs processing similar to that of the second classification unit 103 according to the first exemplary embodiment.

(Processing Flow)

Figure 8:
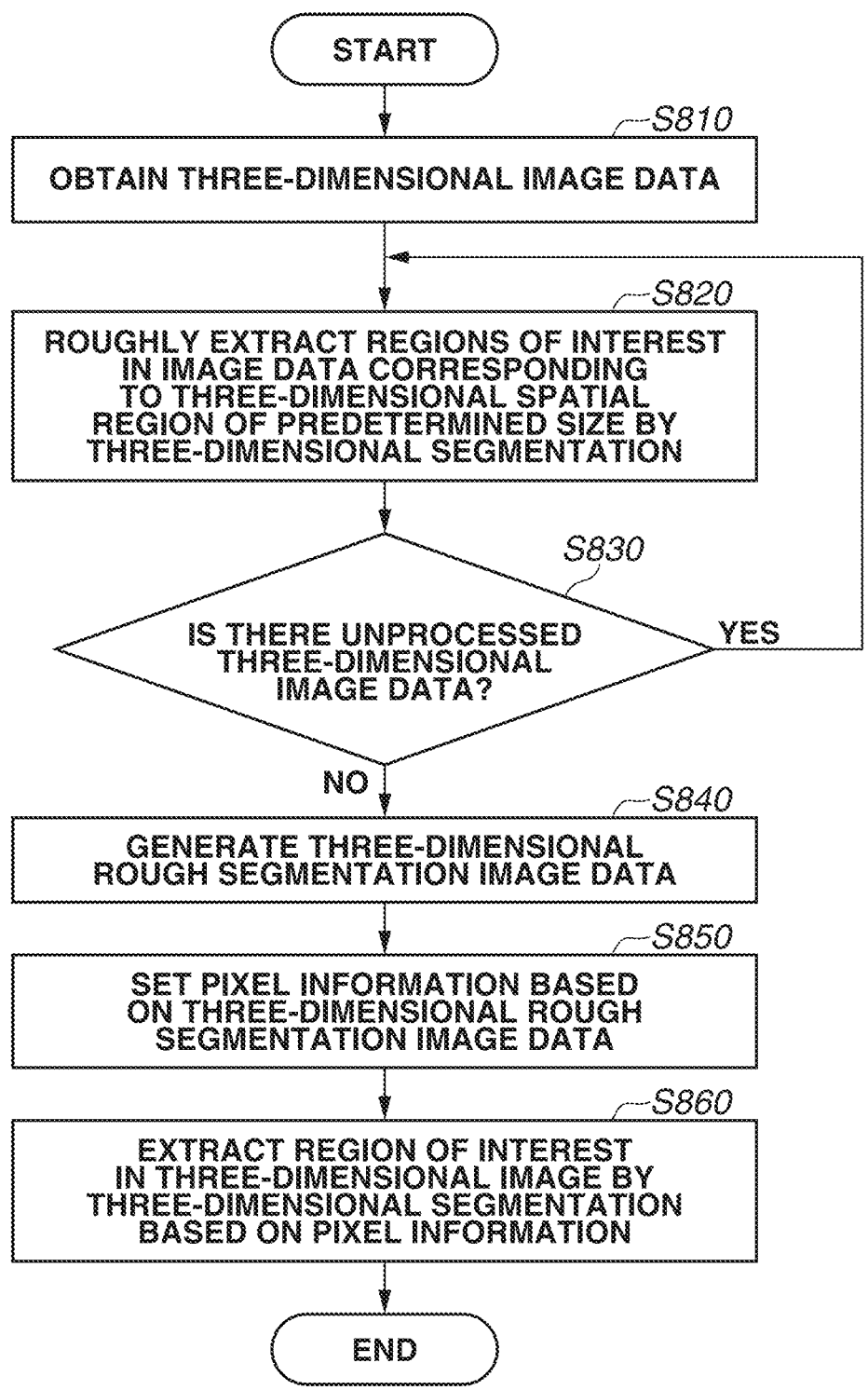
FIG. 8 is a flowchart illustrating an example of a processing procedure of an image processing apparatus according to a second exemplary embodiment.

Next, a processing procedure of the image processing apparatus 100 according to the present exemplary embodiment will be described with reference to FIG. 8.

<Step S810: Three-Dimensional Image Data Obtaining Step>

The processing of step S810 is basically the same as that of step S310 according to the first exemplary embodiment. A description thereof will thus be omitted.

<Step S820: 3D-FCN Based Classification Step>

In step S820, the first classification unit 102 divides the three-dimensional image data into a plurality of three-dimensional spatial regions having the predetermined size, and roughly extracts regions of interest from each of the divided three-dimensional spatial regions by three-dimensional processing. An example of a three-dimensional spatial region having the predetermined size is a set of a predetermined number of continuous axial images in the three-dimensional image data. The result of rough segmentation of the regions of interest by the first classification unit 102 is output as three-dimensional rough segmentation images of the three-dimensional spatial region corresponding to the respective classes in the first class group. Note that the output of the first classification unit 102 may be two-dimensional rough segmentation images.

In the present exemplary embodiment, the first classification unit 102 is a trained 3D-FCN for classifying pixels into the three classes, the liver, the right kidney, and other than the liver and the right kidney. In the present exemplary embodiment, a three-dimensional spatial region having the predetermined size in the three-dimensional image data is an image obtained by stacking three (an example of the predetermined size) continuous axial images in the three-dimensional image data. A rough segmentation image of the three-dimensional spatial region corresponding to each class is a three-dimensional rough segmentation image having the same image size as the three-dimensional spatial region having the predetermined size.

Figure 9A:
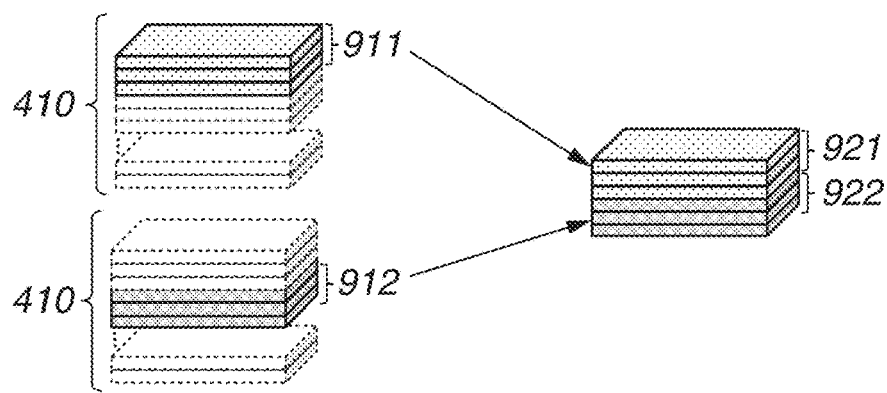
FIG. 9A is a diagram for describing an example of images according to the second exemplary embodiment.
Figure 9B:
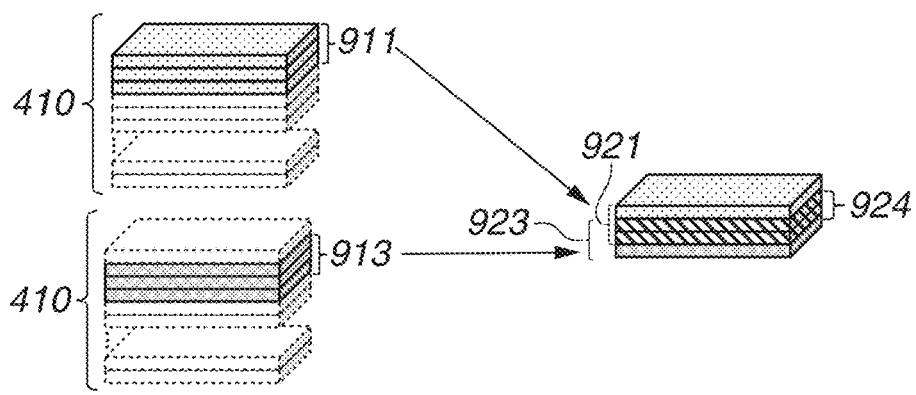
FIG. 9B is a diagram for describing an example of images according to the second exemplary embodiment.

The input and output of the 3D-FCN will be described with reference to FIGS. 9A to 9D. Three-dimensional image data 410 in FIGS. 9A to 9D represents the three-dimensional image data 410 obtained in step S810. For example, each of three-dimensional spatial regions illustrated with different hatchings in FIG. 9A is input to the 3D-FCN according to the present exemplary embodiment. In the diagram, a first three-dimensional spatial region 911 and a second three-dimensional spatial region 912 include three continuous axial images each. Here, the first three-dimensional spatial region 911 and the second three-dimensional spatial region 912 do not include mutually overlapping areas. The 3D-FCN performs the processes illustrated in FIG. 5 on each of the three-dimensional spatial regions, and outputs a first three-dimensional rough segmentation image 921 and a second three-dimensional rough segmentation image 922 corresponding to the three-dimensional spatial regions corresponding to each class. Here, the first three-dimensional rough segmentation image 921 corresponding to the first three-dimensional spatial region 911 and the second three-dimensional rough segmentation image 922 corresponding to the second three-dimensional spatial region 912 are stacked as continuous three-dimensional rough segmentation images. While in the foregoing description the three-dimensional spatial regions of predetermined size into which the three-dimensional image data is divided are described to not include respective mutually overlapping areas, overlapping areas may be included. FIG. 9B illustrates the first three-dimensional spatial region 911 and a second three-dimensional spatial region 913 with overlapping areas. The overlapping areas include two of three continuous axial images. If there are overlapping areas, the output of the first classification unit may be obtained by performing integration processing on the overlapping portions of the rough segmentation images, for example. The integration processing on the overlapping areas may be performed before the softmax processing, for example, or performed after the softmax processing by a method to be described below (described in step S840). If the integration processing is performed before the softmax processing, for example, convolution processing or pixel-by-pixel pooling processing is performed for integration.

<Step S830: Step of Determining Unprocessed Three-Dimensional Spatial Region>

In step S830, the first classification unit 102 determines whether there is an unprocessed three-dimensional spatial region that is not processed in the three-dimensional image data to be processed. If it is determined that there is an unprocessed three-dimensional spatial region, the processing of step S820 is performed on that region. If it is determined that there is no unprocessed three-dimensional spatial region, the processing proceeds to step S840.

<Step S840: Generation of Three-Dimensional Rough Segmentation Image Corresponding to Three-Dimensional Segmentation>

In step S840, the first classification unit 102 performs at least one of stacking, interpolation, and integration processes on the three-dimensional rough segmentation images corresponding to the respective classes of the first class group class by class. The first classification unit 102 generates three-dimensional rough segmentation images corresponding to the respective classes for three-dimensional segmentation purposes by such processing, and transmits the three-dimensional rough segmentation images to the second classification unit 103. In other words, the first classification unit generates the three-dimensional rough segmentation images in making an input to the second classification unit 103, from the plurality of results of classification by the first classification unit 102 corresponding to the three-dimensional spatial regions. There are several variations by which the generation of a three-dimensional rough segmentation image corresponding to each class is implemented.

Figure 9C:
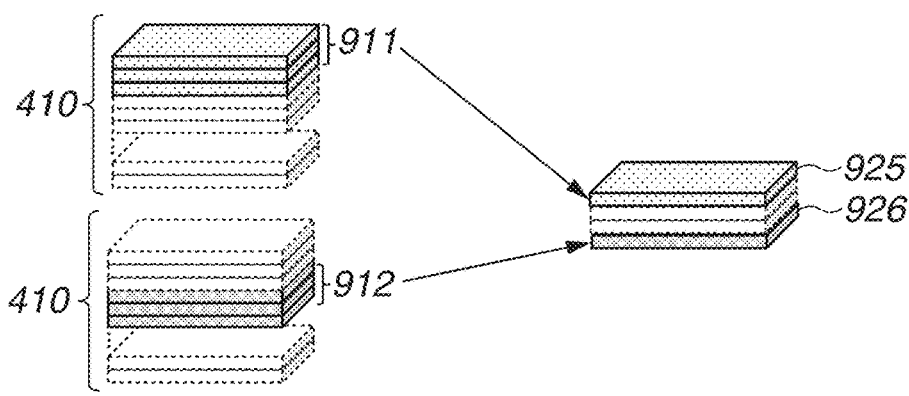
FIG. 9C is a diagram for describing an example of images according to the second exemplary embodiment.
Figure 9D:
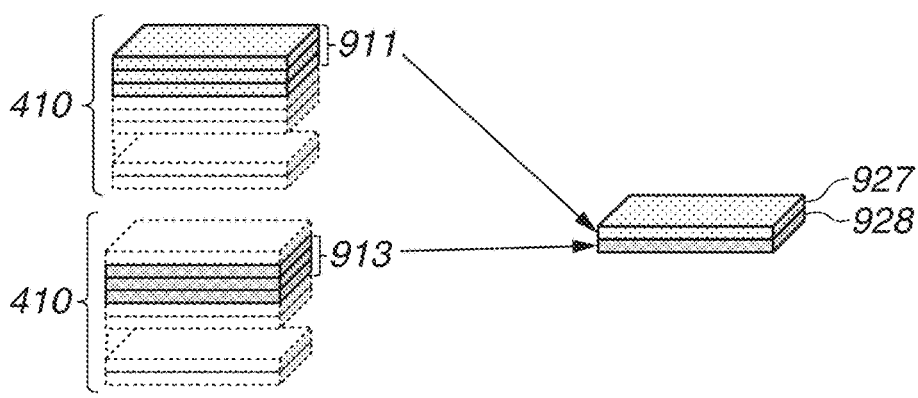
FIG. 9D is a diagram for describing an example of images according to the second exemplary embodiment.

For example, variations of the input to the first classification unit 102 can include cases where there are no overlapping areas as illustrated in FIGS. 9A and 9C and cases where there are overlapping areas as in FIGS. 9B and 9D. Moreover, the cases where there are no overlapping areas can include a case where the first three-dimensional spatial region 911 and the second three-dimensional spatial region 912 are continuous and a case where the first three-dimensional spatial region 911 and the second three-dimensional spatial region 912 are discontinuous.

Variations of the output from the first classification unit 102 can include cases where the three-dimensional rough segmentation image is generated based on all the rough segmentation images output from the 3D-FCN as in FIGS. 9A and 9B and where the three-dimensional rough segmentation image is generated by using each single rough segmentation image selected among the rough segmentation images output from the 3D-FCN as in FIGS. 9C and 9C, for example, among the rough segmentation images corresponding to the three-dimensional spatial regions that are the input. More specifically, there are cases where the three-dimensional rough segmentation image is output from images in which the input images correspond to three-dimensional spatial regions, and where fewer rough segmentation results than the two-dimensional images constituting the three-dimensional spatial regions are output. Note that the number of slices of a selected single rough segmentation image is not limited in particular as long as the number of slices is smaller than the number of slices of a rough segmentation image that is the output from the 3D-FCN. Alternatively, a rough segmentation image generated by performing integration processing based on all the rough segmentation images corresponding to the three-dimensional spatial regions may be used.

A case where the first three-dimensional spatial region and the second three-dimensional spatial region that are the input are continuous regions with no overlapping areas and the three-dimensional rough segmentation image is generated by using all the rough segmentation images that are the output of the 3D-FCN will initially be described with reference to FIG. 9A. In such a case, all the slices of the first three-dimensional rough segmentation image 921 and the second three-dimensional rough segmentation image 922 are simply stacked to generate the three-dimensional rough segmentation image, which is input to the second classification unit 103.

Next, a case with a first two-dimensional rough segmentation image 925 corresponding to the first three-dimensional spatial region 911 and a second two-dimensional rough segmentation image 926 corresponding to the second three-dimensional spatial region 912 will be described with reference to FIG. 9C. The three-dimensional rough segmentation image is generated by using a predetermined number of rough segmentation images among the rough segmentation images corresponding to the respective three-dimensional spatial regions having the predetermined size, classified by the first classification unit 102. A method for generating a three-dimensional rough segmentation image by using a single rough segmentation image selected from or obtained by performing integration processing on the rough segmentation images of each input three-dimensional spatial region will now be described. The single rough segmentation image may be a rough segmentation image at the center of all the rough segmentation images corresponding to the three-dimensional spatial region having the predetermined size, or one obtained by average integration of averaging the pixel values of all the rough segmentation images corresponding to the three-dimensional spatial region. Alternatively, the single rough segmentation image may be generated by performing maximum value integration using the maximum values among the pixel values of all the rough segmentation images corresponding to the three-dimensional spatial region. The average integration or the maximum value integration does not need to be targeted for all the slices constituting the rough segmentation images of the three-dimensional space region having the predetermined size. For example, an integration process may be performed on a plurality of rough segmentation images among all the rough segmentation images corresponding to the three-dimensional spatial region. Different integration processes may be performed on a plurality of rough segmentation images. An integration process may be performed on each of a plurality of rough segmentation images a plurality of times. The generated first two-dimensional rough segmentation image 925 and the generated second two-dimensional rough segmentation image 926 are subject to at least one of mutual stacking, interpolation processing, and integration processing, whereby the three-dimensional rough segmentation image is generated.

Next, a case will be described where the first three-dimensional spatial region and the second three-dimensional spatial region that are the input to the first classification unit 102 are discontinuous regions with no overlapping areas and the output is a three-dimensional rough segmentation image corresponding to each class or two-dimensional rough segmentation images corresponding to a three-dimensional spatial region having the predetermined size. If all the rough segmentation images extracted by the 3D-FCN are used, at least one of stacking, interpolation, and integration processes is performed on both the rough segmentation images corresponding to the first three-dimensional spatial region and the rough segmentation images corresponding to the second three-dimensional spatial region, whereby the three-dimensional rough segmentation image is generated. The step of generating the three-dimensional rough segmentation image from the two-dimensional rough segmentation images corresponding to the three-dimensional spatial regions having the predetermined size is similar to the foregoing.

Finally, the cases where the inputs to the first classification unit 102 include overlapping areas as illustrated in FIGS. 9B and 9D will be described. FIG. 9B includes the rough segmentation image 921 corresponding to the first three-dimensional spatial region 911 having the predetermined size and the rough segmentation image 923 corresponding to the second three-dimensional spatial region 913 having the predetermined size. The rough segmentation image 921 and the rough segmentation image 923 include an overlapping area 924 each. In such a case, average integration or maximum value integration may be applied to the overlapping areas 924. At least one of stacking, interpolation, and integration processes may be performed between the rough segmentation images to generate a three-dimensional rough segmentation image. In FIG. 9D, the first three-dimensional spatial region 911 and the second three-dimensional spatial region 913 have overlapping areas. Here, the first three-dimensional spatial region 911 corresponds to a two-dimensional rough segmentation image 927, and the second three-dimensional spatial region 913 corresponds to a two-dimensional rough segmentation image 928. A rough segmentation image is generated from each of the rough segmentation images corresponding to the three-dimensional spatial regions having the predetermined size. The number of rough segmentation images generated from each of the rough segmentation images corresponding to the three-dimensional spatial regions does not need to be one as long as the number is smaller than the number of slices constituting a three-dimensional spatial region having the predetermined size. The single rough segmentation image to be generated may be obtained by performing interpolation, stacking, or integration processing on the rough segmentation images corresponding to the three-dimensional spatial regions having the predetermined size. The step of generating the three-dimensional rough segmentation image from the two-dimensional rough segmentation images corresponding to the three-dimensional spatial regions having the predetermined size is similar to the foregoing. Moreover, in the present configuration, the connectivity between the three-dimensional spatial regions can be taken into account by adjusting the number of slices generated from each three-dimensional spatial region having the predetermined size and the number of not-overlapping slices.

<Step S850: Pixel Information Setting Step>

The processing of step S850 is basically the same as that of step S350 according to the first exemplary embodiment. A description thereof will thus be omitted.

<Step S860: Step of Extracting Region of Interest by Graph-Cut Method>

The processing of step S860 is basically the same as that of step S360 according to the first exemplary embodiment. A description thereof will thus be omitted.

Effect of Second Exemplary Embodiment

As described above, the image processing apparatus 100 according to the second exemplary embodiment divides three-dimensional image data into a plurality of three-dimensional spatial regions having a predetermined size, and roughly extracts regions of interest from each of the three-dimensional spatial regions. Such a configuration improves the accuracy of the result of rough segmentation of the regions of interest since the first classification unit 102 can take three-dimensional connectivity into account. The effect contributes to improved accuracy of segmentation of the region of interest by the second classification unit 103.

Modification

In the foregoing image processing apparatus 100 according to the second exemplary embodiment, the first classification unit 102 uses only three-dimensional spatial regions having the predetermined size in the three-dimensional image data as its input. However, other information about the regions of interest may be input at the same time. Here, the input refers to training data in training the classifier and three-dimensional image data input to the first classification unit. For example, the result of segmentation of the regions of interest from adjoining three-dimensional spatial regions may be input at the same time. An existence probability map of the regions of interest estimated by another method and/or bounding boxes including the regions of interest may be input. Such a configuration improves the accuracy of the result of rough segmentation of the regions of interest by the first classification unit since the first classification unit 102 can further use region of interest information about other regions and information about the regions of interest estimated by another method. This effect contributes to improved accuracy of segmentation of the region of interest by the second classification unit 103. Such pieces of additional information are also available to the second classification unit 103. Giving additional information intended for the second classification unit to the pixel information to generate a seed image is expected to enable more precise segmentation of the region of interest. The additional information may be given to only the first classification unit, only the second classification unit, or both the classification units. This modification is not limited to only the second exemplary embodiment, and is also effective for the first exemplary embodiment.

OTHER EXEMPLARY EMBODIMENTS

The present invention is also implemented by executing the following processing. The processing includes supplying software (program) for implementing the functions of the foregoing exemplary embodiments to a system or an apparatus via a network or various storage media, and reading and executing the program by a computer (or CPU, MPU, or the like) of the system or apparatus.

The present invention is not limited to the above embodiments and various changes and modifications can be made within the spirit and scope of the present invention. Therefore, to apprise the public of the scope of the present invention, the following claims are made.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the image processing apparatus according to the present invention, the user's burden of giving pixel information can be reduced and a region can be extracted with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing a program; and
one or more processors which, by executing the program, function as:
a first classification unit configured to classify a plurality of pixels in each of a plurality of pieces of two-dimensional image data constituting first three-dimensional image data including an object into a first class group by using a trained classifier, wherein the first classification unit further includes a three-dimensional data generation unit configured to generate a three-dimensional result of classification by classifying the plurality of pixels in each of the plurality of pieces of two-dimensional image data constituting the first three-dimensional image data into the first class group; and
a second classification unit configured to classify a plurality of pixels in second three-dimensional image data including the object into a second class group based on the three-dimensional result of classification by the first classification unit, the second class group including at least one class of the first class group.

2. The image processing apparatus according to claim 1, wherein the three-dimensional data generation unit is configured to generate the three-dimensional result of classification by performing at least one of stacking, interpolation, and integration processes on the result of classification of each of the plurality of pieces of two-dimensional image data by the first classification unit.

3. The image processing apparatus according to claim 1, wherein the two-dimensional image data is axial image data.

4. The image processing apparatus according to claim 1, wherein the first three-dimensional image data and the second three-dimensional image data are medical image data.

5. The image processing apparatus according to claim 1, wherein the first class group includes a class representing a liver and a class representing a kidney.

6. The image processing apparatus according to claim 1, wherein the second class group includes a class representing a liver.

7. The image processing apparatus according to claim 1, wherein the second classification unit is configured to classify the plurality of pixels in the second three-dimensional image data into the second class group by a graph-cut method.

8. The image processing apparatus according to claim 1, wherein the result of classification by the first classification unit includes likelihood of a class constituting the first class group.

9. The image processing apparatus according to claim 8, further comprising an obtaining unit configured to obtain region information indicating a foreground, a background, and an intermediate region corresponding to neither of the foreground and the background based on the likelihood,
wherein the second classification unit is configured to, based on the likelihood and the region information,
set first energy for a pixel corresponding to the foreground,
set second energy for a pixel corresponding to the background,
set third energy for a pixel corresponding to the intermediate region, the third energy corresponding to the likelihood at the pixel, and
classify the plurality of pixels in the second three-dimensional image data into the second class group by a graph-cut method using the first energy, the second energy, and the third energy.

10. The image processing apparatus according to claim 1, wherein the first three-dimensional image data and the second three-dimensional image data are same three-dimensional image data.

11. The image processing apparatus according to claim 1, wherein the first three-dimensional image data and the second three-dimensional image data are different pieces of three-dimensional image data.

12. The image processing apparatus according to claim 11, wherein the first three-dimensional image data has resolution lower than that of the second three-dimensional image data.

13. The image processing apparatus according to claim 11, wherein the first three-dimensional image data and the second three-dimensional image data are pieces of three-dimensional image data linked with a same test subject and having different imaging times.

14. The image processing apparatus according to claim 1, wherein the trained classifier includes at least one of a CNN, an SVM, and a k-means model.

15. The image processing apparatus according to claim 1, wherein the trained classifier is a CNN having a network structure using an encoder and a decoder.

16. The image processing apparatus according to claim 1, wherein the second classification unit is configured to classify the plurality of pixels in the second three-dimensional image data into the second class group by at least one of a graph-cut method, a level-set method, a region growing method, and a snake method.

17. The image processing apparatus according to claim 1, wherein the first classification unit is configured to classify a plurality of pixels in each of two-dimensional image data constituting first three-dimensional image data including the object into the first class group by using the trained classifier.

18. An image processing apparatus comprising:
a memory storing a program; and
one or more processors which, by executing the program, function as:
a first classification unit configured to classify each of a plurality of voxels corresponding to a first three-dimensional spatial region having a predetermined size in first three-dimensional image data including an object into a first class group by using a trained classifier, and classify each of a plurality of voxels corresponding to a second three-dimensional spatial region having the predetermined size into the first class group; and
a second classification unit configured to classify at least one voxel included in second three-dimensional image data including the object into a second class group based on a result of classification of the plurality of voxels corresponding to the first three-dimensional spatial region and a result of classification of the plurality of voxels corresponding to the second three-dimensional spatial region, the second class group including at least one class of the first class group.

19. The image processing apparatus according to claim 18, wherein a result of classification of a region different from the first three-dimensional spatial region or the second three-dimensional spatial region by the first classification unit is further input to the first classification unit.

20. The image processing apparatus according to claim 18, wherein the first three-dimensional spatial region and the second three-dimensional spatial region do not overlap each other.

21. The image processing apparatus according to claim 18, further comprising a three-dimensional data generation unit configured to generate a three-dimensional result of classification by performing at least one of stacking, interpolation, and integration processes on the result of classification of the plurality of voxels corresponding to the first three-dimensional spatial region and the result of classification of the plurality of voxels corresponding to the second three-dimensional spatial region,
wherein the second classification unit is configured to classify the at least one voxel included in the second three-dimensional image data into the second class group based on the three-dimensional result of classification.

22. The image processing apparatus according to claim 18, wherein the first three-dimensional spatial region and the second three-dimensional spatial region include mutually overlapping areas.

23. The image processing apparatus according to claim 22, further comprising a three-dimensional data generation unit configured to generate a three-dimensional result of classification by integrating results of classification corresponding to the overlapping areas by the first classification unit,
wherein the second classification unit is configured to classify the at least one voxel included in the second three-dimensional image data into the second class group based on the three-dimensional result of classification.

24. The image processing apparatus according to claim 18, wherein the first three-dimensional spatial region and the second three-dimensional spatial region include a plurality of pieces of axial image data each.

25. An image processing method comprising:
classifying a plurality of pixels in each of a plurality of pieces of two-dimensional image data constituting first three-dimensional image data including an object into a first class group by using a trained classifier;
generating a three-dimensional result of classification by classifying the plurality of pixels in each of the plurality of pieces of two-dimensional image data constituting the first three-dimensional image data into the first class group; and
classifying a plurality of pixels in second three-dimensional image data including the object into a second class group based on the three-dimensional result of classification into the first class group, the second class group including at least one class of the first class group.

26. A storage medium storing a program for causing a computer to perform the image processing method according to claim 25.

27. An image processing method comprising:
classifying as a first classification each of a plurality of voxels corresponding to a first three-dimensional spatial region having a predetermined size in first three-dimensional image data including an object into a first class group by using a trained classifier;
classifying as a first classification each of a plurality of voxels corresponding to a second three-dimensional spatial region having the predetermined size into the first class group; and
classifying as a second classification at least one voxel included in second three-dimensional image data including the object into a second class group based on a result of classification of the plurality of voxels corresponding to the first three-dimensional spatial region and a result of classification of the plurality of voxels corresponding to the second three-dimensional spatial region, the second class group including at least one class of the first class group.

28. An image processing system comprising:
a memory storing a program; and
one or more processors which, by executing the program, function as:
a first classification unit configured to classify a plurality of pixels in each of a plurality of pieces of two-dimensional image data constituting first three-dimensional image data including an object into a first class group by using a trained classifier, wherein the first classification unit further includes a three-dimensional data generation unit configured to generate a three-dimensional result of classification by classifying the plurality of pixels in each of the plurality of pieces of two-dimensional image data constituting the first three-dimensional image data into the first class group; and
a second classification unit configured to classify a plurality of pixels in second three-dimensional image data including the object into a second class group based on the three-dimensional result of classification by the first classification unit, the second class group including at least one class of the first class group.

29. An image processing system comprising:

a memory storing a program; and one or more processors which, by executing the program, function as:

a first classification unit configured to classify each of a plurality of voxels corresponding to a first three-dimensional spatial region having a predetermined size in first three-dimensional image data including an object into a first class group by using a trained classifier, and classify each of a plurality of voxels corresponding to a second three-dimensional spatial region having the predetermined size into the first class group; and a second classification unit configured to classify at least one voxel included in second three-dimensional image data including the object into a second class group based on a result of classification of the plurality of voxels corresponding to the first three-dimensional spatial region and a result of classification of the plurality of voxels corresponding to the second three-dimensional spatial region, the second class group including at least one class of the first class group.

* * * * *